United States Patent [19]
Yoshioka et al.

[11]  4,269,705
[45]  May 26, 1981

[54] METHOD FOR REMOVING CHROMIUM IONS FROM AQUEOUS SOLUTIONS OF ORGANIC ACIDS

[75] Inventors: Teruhiko Yoshioka; Hideo Matsuzawa; Kazuya Okada, all of Otake; Minoru Ikeda, Saiki, all of Japan

[73] Assignee: Mitsubishi Rayon Co., Ltd., Tokyo, Japan

[21] Appl. No.: 31,157

[22] Filed: Apr. 18, 1979

[51] Int. Cl.$^3$ .............................................. B01D 15/04
[52] U.S. Cl. ..................................... 562/600; 423/54; 562/606; 562/608; 526/609; 210/688
[58] Field of Search ........... 210/31 C, 38 B, DIG. 30; 423/54; 562/600, 606, 608, 609

[56] References Cited

U.S. PATENT DOCUMENTS

| | | | |
|---|---|---|---|
| 3,681,210 | 8/1972 | Zievers et al. | 210/38 B |
| 3,819,799 | 6/1974 | Matschke et al. | 210/38 B |
| 3,972,810 | 8/1976 | Chopra | 210/38 B |

*Primary Examiner*—Ivars C. Cintins
*Attorney, Agent, or Firm*—Oblon, Fisher, Spivak, McClelland & Maier

[57] ABSTRACT

A method of removing chromium ion from an aqueous solution of an organic acid of an acid concentration of up to 95% which comprises treating the solution with a cation exchange resin at a temperature higher than 55° C.

7 Claims, No Drawings

METHOD FOR REMOVING CHROMIUM IONS FROM AQUEOUS SOLUTIONS OF ORGANIC ACIDS

BACKGROUND OF THE INVENTION

1. Field of the Invention

This invention relates to a method of efficiently removing chromium ions from an aqueous solution of an organic acid containing chromium.

2. Description of the Prior Art

An aqueous solution of an organic acid is often handled industrially by using an apparatus made of stainless steel.

The recovery of such organic acids from an aqueous solution containing them has been carried out by extraction and distillation operations. When the acid is in aqueous solution it has been known to produce tert-butyl alcohol by reacting the water with isobutylene and separating the acid. These methods are mentioned in Japanese patent application Nos. 32116 and 126603/1975.

In these cases, however, depending on the operating conditions, such metals as iron, nickel and chromium may dissolve in the liquid mixtures, due to the corrosion of the stainless steel material, thus contaminating the final products. It is often required to remove such contaminating metals, usually for the prevention of the poisoning and toxicity of catalysts or for other related reasons. For example, in the methods mentioned in the above described Japanese published patent application Nos. 32116 and 126603/1975, the metallic ions in a circulating aqueous solution of an organic acid are removed. When such removal of metallic ions is necessary, a usual method would be to remove the metals by ion exchange chromatography using a cation exchange resin. When the present inventors attempted to remove such metallic ions by standard ion exchange methods they unexpectedly encountered the problem that while iron and nickel may be removed chromium is hardly removed, if at all.

As a result of continuing investigation of this problem, the present inventors have discovered an improved process for solving the separation problems of prior art methods.

SUMMARY OF THE INVENTION

It is therefore an object of the invention to provide a method for the purification of aqueous solutions of organic acids.

It is another object of the invention to provide an efficient method for the separation of chromium ions from aqueous solutions of organic acids.

It is a further object of the invention to provide an ion exchange method for the separation of chromium ions from aqueous solutions of organic acids.

These and other objects of the invention have been obtained by providing a method of removing chromium ions from an aqueous solution of an organic acid, of an acid concentration of up to 95%, which comprises treating said solution with a cation exchange resin at a temperature higher than 55° C.

DESCRIPTION OF THE PREFERRED EMBODIMENTS

When an organic acid is used in 100% concentration, chromium ions are comparatively well ion-exchanged but, when using an aqueous solution of an organic acid, chromium ion are very hard to ion-exchange. The ease or difficulty of the ion exchange of chromium ion from such aqueous solutions depends remarkably on the temperature. The higher the temperature of separation, the easier the ion-exchange of chromium will be from aqueous solutions of organic acids.

It has been found that, though the temperature effects depend somewhat on the kind of organic acid, aqueous solutions of common organic acids containing Cr ion yield, when ion-exchanged at room temperature, little ion-exchange of chromium ion but, above 55° C. and particularly above 70° to 80° C., the velocity of the chromium ion exchange becomes remarkably high. The exchanged amount of chromium is also large and the chromium removing effect is high.

Any common acid in aqueous solution can be purified by the method of the present invention, such as formic, acetic, propionic, butyric, and higher alkanoic acids; unsaturated acids such as acrylic, methacrylic acids; aromatic acids, such as benzoic or toluic; or mixtures thereof. The present invention is thus characterized by treating and removing chromium ion from an aqueous solution of an organic acid of up to 95% concentration at a temperature above 55° C. by using an ion exchange resin. Standard cation exchange resins can be used in the present invention, such as those described at pp. 618–622 of "Chemical and Process Technology Encyclopedia," edited by D. M. Considine, McGraw-Hill, 1974. For example, strong acid resins such as sulfonate-containing resins may be used, or weak acid resins, such as carboxylic or phosphonic acid resins may also be used. The resin can be used batchwise or in a column.

In the present invention, the chromium removing effect becomes important at temperatures above 55° C. However, at higher temperatures, the effect becomes more remarkable and, particularly, above 70° C., the effect is quite high. The upper limits of temperature are determined by the boiling point and volatility of the aqueous solutions being exchanged, as well as the probable decomposition of resin.

The preferred concentrations of the organic acid in aqueous solution is up to 95%, most preferably up to 85%.

Having generally described this invention, a further understanding can be obtained by reference to certain specific examples which are provided herein for purposes of illustration only and are not intended to be limiting unless otherwise specified.

EXAMPLE 1

(1) Relation of the chromium ion removal to acetic acid concentration

Aqueous solutions of acetic acid of various concentrations containing chromium acetate (containing 595 ppm as of chromium) and an acetic acid solution were prepared and were passed at S.V. (space velocity)=2 at a room temperature (of 27° C.) through a layer charged with 5 ml of a strong acid cationic exchange resin (*). The results are shown in Table 1.

*Amberlite 200C which is referred to as IR-200 hereinafter

TABLE 1

| Acetic Acid concentration (%) by weight | 0 | 10 | 30 | 50 | 70 | 85 | 95 | 100 |
|---|---|---|---|---|---|---|---|---|
| Amount of the solution passed until chromium | | about 10 | | | | | about | about |

TABLE 1-continued

| Acetic Acid concentration (%) by weight | 0 | 10 | 30 | 50 | 70 | 85 | 95 | 100 |
|---|---|---|---|---|---|---|---|---|
| ion began to leak (ml) | | | | | | | 110 | 180 |

The theoretical ion-exchangeable amount of the solution is about 220 ml.

It can be seen from these results that, in the case of an aqueous solution of acetic acid of concentration less than 85%, chromium ion begins leaking almost immediately. In the case of 100% acetic acid, the ion exchange will be possible up to 180 ml near the theoretical amount of 220 ml before leaking starts. In the case of an aqueous solution of 95% acetic acid, the ion exchange will be intermediate between these 2 values.

It can thus be recognized that, in the case of an aqueous solution of up to 95% acetic acid, chromium ion will be remarkably hard to ion-exchange.

(2) Relation of chromium ion removed to temperature

An aqueous solution of 85% acetic acid containing chromium acetate (containing 595 ppm as chromium) was passed at S.V.=4 at various temperatures through a layer charged with 5 ml of a strong acid cation exchange resin (IR-200).

The results of measuring the amounts of the solution passed until the start of chromium leak are shown in Table 2.

TABLE 2

| Temperature (°C.) | 30 | 40 | 50 | 55 | 60 | 70 | 80 |
|---|---|---|---|---|---|---|---|
| Amount of the solution passed until start of chromium leak (ml) | about 10 | 20 | 30 | 90 | 110 | 150 | 210 |

It is found from these results that the ease or difficulty of the ion exchange of chromium ion is remarkably influenced by the temperature. At temperatures above 55° C., the effect is particularly high. Particularly, in the case of 80° C., it is possible to exchange substantially up to the theoretical exchanging capacity (of an amount of about 220 ml of the solution).

EXAMPLE 2

When the removal of chromium ion (contained by 500 ppm) in an aqueous solution of 85% methacrylic acid using methacrylic acid as an organic acid was attempted at 25° C. after passage of 10 ml of the aqueous solution, 108 ppm of chromium leaked. At 55° C. however, 24 ppm leaked and, at 80° C., only up to 2 ppm leaked.

EXAMPLES 3-5

An aqueous solution of 85% acetic acid containing chromium acetate (containing 595 ppm as of chromium) was passed at S.V.=4 at temperatures of 55°, 70° and 80° C. through a layer charged with 5 ml of a strong acid cation exchange resin (IR-200).

The amounts of the solution passed until chromium ion began to leak are shown in Table 3.
Controls 3' to 5':

Controls corresponding to experiments 3-5 were carried out under the same conditions but at temperatures of 30°, 40° and 50° C. These are also shown in Table 3.

TABLE 3

| | Temperature (°C.) | Amount of the solution passed until chromium ion began to leak (ml) |
|---|---|---|
| Example 3 | 80 | about 210 |
| 4 | 70 | 150 |
| 5 | 55 | 90 |
| Controls 3' | 50 | about 30 |
| 4' | 40 | 20 |
| 5' | 30 | 10 |

As evident from the above mentioned examples and controls, at a temperature above 55° C., it will be easy to remove chromium ion.

EXAMPLES 6 to 9

An aqueous solution of acetic acid of acetic acid concentrations of 10, 50, 70 and 95% containing chromium acetate (595 ppm as of chromium) was passed at S.V.=2 at 80° C. through a layer charged with 5 ml of IR-200.

The results are shown in Table 4.
Controls 6' to 9':

The same experiments as in Examples 6 to 9 were carried out at a temperature of 27° C., and the results are also shown in Table 4.

TABLE 4

| | Acetic acid concentration | Temperature | Amount of the solution passed until chromium ion began to leak |
|---|---|---|---|
| Example 6 | 10% | 80° C. | about 210 ml |
| 7 | 50 | 80 | 210 |
| 8 | 70 | 80 | 210 |
| 9 | 95 | 80 | 210 |
| Control 6' | 10% | 27° C. | about 10 ml |
| 7' | 50 | 27 | 10 |
| 8' | 70 | 27 | 10 |
| 9' | 95 | 27 | 10 |

As evident from the above mentioned examples and controls, even if the same acetic acid concentrations are compared, the effects of the present invention can still be clearly observed.

EXAMPLES 10 to 13

Chromium salts of formic acid, propionic acid, acrylic acid and methacrylic acid were dissolved in an aqueous solution of 85% of the corresponding organic acid (containing a concentration of 595 ppm as chromium).

These solutions were passed at S.V.=4 at a temperature of 80° C. through a layer charged with 5 ml of IR-200.

The results are shown in Table 5.
Controls 10' to 13':

The same experiments as in Examples 8 to 11 were carried out at a temperature of 27° C. and the results are also shown in Table 5.

TABLE 5

| | Organic acid | Temperature | Amount of the solution passed until chromium ion began to leak |
|---|---|---|---|
| Example 10 | Formic acid | 80° C. | |
| 11 | Propionic acid | 80 | |
| 12 | Acrylic acid | 80 | about 210 ml |
| 13 | Methacrylic acid | 80 | |
| Control 10' | Formic acid | 27° C. | |
| 11' | Propionic acid | 27 | 10 ml at most |

TABLE 5-continued

| Organic acid | Temperature | Amount of the solution passed until chromium ion began to leak |
|---|---|---|
| 12' Acrylic acid | 27 | |
| 13' Methacrylic acid | 27 | |

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A method of removing chromium ions from an aqueous solution of an organic acid having an acid concentration of up to 95%, which comprises treating said solution with a cation exchange resin at a temperature higher than 55° C.

2. A method according to claim 1 wherein said organic acid is selected from the group consisting of formic acid, acetic acid, propionic acid, acrylic acid and methacrylic acid.

3. A method according to claim 1 wherein said aqueous solution of an organic acid is an aqueous solution of acetic acid of up to 85% acetic acid.

4. A method according to any of claims 1, 2 or 3 wherein the temperature is higher than 70° C.

5. A method according to claim 1 wherein the cation exchange resin is a strong acid resin.

6. A method according to claim 1 wherein the resin is used batchwise.

7. A method according to claim 1 wherein the resin is loaded in a chromatographic column.

* * * * *